(12) United States Patent
Hock et al.

(10) Patent No.: US 7,074,899 B2
(45) Date of Patent: Jul. 11, 2006

(54) HUMAN EPHA9 RECEPTOR POLYPEPTIDES

(75) Inventors: Bjoern Hock, Maintal (DE); Klaus Duecker, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 76 days.

(21) Appl. No.: 10/333,789

(22) PCT Filed: Jul. 17, 2001

(86) PCT No.: PCT/EP01/08210

§ 371 (c)(1),
(2), (4) Date: Jan. 24, 2003

(87) PCT Pub. No.: WO02/08253

PCT Pub. Date: Jan. 31, 2002

(65) Prior Publication Data

US 2004/0072747 A1    Apr. 15, 2004

(51) Int. Cl.
*C07K 14/435* (2006.01)
(52) U.S. Cl. .................................................... 530/350
(58) Field of Classification Search ................ 530/350; 514/2; 435/69.1
See application file for complete search history.

(56) References Cited

U.S. PATENT DOCUMENTS 5,639,597 A * 6/1997 Lauffer et al. .................. 435/5
2003/0096952 A1 * 5/2003 Majumder et al. .......... 530/350

FOREIGN PATENT DOCUMENTS

WO    WO 99 52541 A3    10/1999

OTHER PUBLICATIONS

Majumder K et al., GenBank Accession No. CAD13085 and alignment of CAD13085 with SEQ ID No. 1.*
Himanen et al. (2003), Int. J. Biochem. Cell Biol. 35: 130-134.*
Lee et al. (1996), DNA Cell Biol. 15(10): 817-825.*
Mellitzer et al. (2000), Cur. Opin. Neurobiol. 10: 400-408.*
Matsunaga et al. (2000), Eur. J. Neurosci. 12: 1599-1616.*
Bruckner et al. (1998) Cur. Opin. Neurobiol. 8: 375-382.*
U.S. Appl. No. 60/195,343, filed on Apr. 5, 2000.*
Ji et al. (1998), J. Biol. Chem., 273: 17299-17302.*
Skolnick et al. (2000), Trends in Biotech. 18: 34-39.*
Bork (2000), Genome Research 10: 398-400.*
Doerks et al. (1998), Trends in Genetics 14: 248-250.*
Mickle JE et al. Genotype-phenotype relationships in cystic fibrosis. Med Clin North Am. May 2000; 84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Fox et al., "cDNA cloning and tissue distribution of five human EPH-like receptor protein-tyrosine kinases," *Oncogene*, No. 10, 1995, pp. 897-905, XP000946743.
Gale et al., "EpH receptors and ligands comprise two major specificity subclasses and are reciprocally compartmentalized during embryogenesis," *Neuron*, vol. 17, Jul. 1996, pp. 9-19, XP002048874.
Holland et al., "Juxtamembrane tyrosine residues couple the Eph family receptor EphB2/Nuk to specific SH2 domain proteins in neuronal cells," *The EMBO Journal*, vol. 16, No. 13, 1997, pp. 3877-3888, XP002188451.

* cited by examiner

*Primary Examiner*—Ruixiang Li
(74) *Attorney, Agent, or Firm*—Millen, White, Zelano & Branigan, P.C.

(57) ABSTRACT

EphA9 polypeptides and polynucleotides and methods for producing such polypeptides by recombinant techniques are disclosed. Also disclosed are methods for utilizing EphA9 polypeptides and polynucleotides in diagnostic assays.

7 Claims, No Drawings

SEQUENCE LISTING

```
<160> NUMBER OF SEQ ID NOS: 2

<210> SEQ ID NO 1
<211> LENGTH: 2400
<212> TYPE: DNA
<213> ORGANISM: Homo sapiens
<220> FEATURE:
<221> NAME/KEY: CDS
<222> LOCATION: (75)..(2147)

<400> SEQUENCE: 1
tacatcactg tctgttaaag gaaaccaagc gtgaagtgga agtctaacac atgaggatac       60
agaattgatt caaa atg gga aca aca agt gat gag atg gtg tct gtg gaa      110
```

```
                Met Gly Thr Thr Ser Asp Glu Met Val Ser Val Glu
                 1               5                  10 cag acc tcc tcc tct tct cta aac ccc ctg tgt ttt gaa tgt ggc caa           158
Gln Thr Ser Ser Ser Ser Leu Asn Pro Leu Cys Phe Glu Cys Gly Gln
         15                  20                  25 cag cac tgg aca aga gaa aac cat ttg tac aat tac cag aat gaa gtg           206
Gln His Trp Thr Arg Glu Asn His Leu Tyr Asn Tyr Gln Asn Glu Val
     30                  35                  40 gat gat gac cta gtc tgc cat att tgc ctt caa cct ctg ctg cag cca           254
Asp Asp Asp Leu Val Cys His Ile Cys Leu Gln Pro Leu Leu Gln Pro
 45                  50                  55                  60 cta gac aca ccc tgt gga cat aca ttc tgc tac aag tgc ctc aga aac           302
Leu Asp Thr Pro Cys Gly His Thr Phe Cys Tyr Lys Cys Leu Arg Asn
                 65                  70                  75 ttt tta caa gag aaa gat ttc tgt ccg ttg gac cgg aaa aga ctt cat           350
Phe Leu Gln Glu Lys Asp Phe Cys Pro Leu Asp Arg Lys Arg Leu His
             80                  85                  90 ttt aag ttg tgc aag aag tct agt att cta gtt cat aaa ctc cta gac           398
Phe Lys Leu Cys Lys Lys Ser Ser Ile Leu Val His Lys Leu Leu Asp
         95                 100                 105 aaa tta tta gtt tta tgt cca ttt tct tca gtg tgc aaa gat gta atg           446
Lys Leu Leu Val Leu Cys Pro Phe Ser Ser Val Cys Lys Asp Val Met
     110                 115                 120 caa cgt tgt gat ctg gag gca cat ctc aaa aac aga tgt cct gga gct           494
Gln Arg Cys Asp Leu Glu Ala His Leu Lys Asn Arg Cys Pro Gly Ala
125                 130                 135                 140 tct cat cgg aga gtt gcc ctg gag aga agg aaa act agt aga act caa           542
Ser His Arg Arg Val Ala Leu Glu Arg Arg Lys Thr Ser Arg Thr Gln
                145                 150                 155 gca gag att gag aat gaa aat ggg ccc act cta cta gat cct gca ggt           590
Ala Glu Ile Glu Asn Glu Asn Gly Pro Thr Leu Leu Asp Pro Ala Gly
            160                 165                 170 acc tta tct cca gaa gca gac tgt ttg ggg aca ggc gca gtg cct gtg           638
Thr Leu Ser Pro Glu Ala Asp Cys Leu Gly Thr Gly Ala Val Pro Val
        175                 180                 185 gag cgg cac ttg aca tca gcg tct ctt tcc aca tgg agt gag gag cct           686
Glu Arg His Leu Thr Ser Ala Ser Leu Ser Thr Trp Ser Glu Glu Pro
    190                 195                 200 ggc ctt gac aac cct gcc ttt gag gag agc gct gga gct gac acc aca           734
Gly Leu Asp Asn Pro Ala Phe Glu Glu Ser Ala Gly Ala Asp Thr Thr
205                 210                 215                 220 caa cag cca ctt agt tta cca gaa gga gaa atc acc acg att gaa att           782
Gln Gln Pro Leu Ser Leu Pro Glu Gly Glu Ile Thr Thr Ile Glu Ile
                225                 230                 235 cat cgg tcc aat cct tac att cag tta gga atc agc att gtg ggt ggc           830
His Arg Ser Asn Pro Tyr Ile Gln Leu Gly Ile Ser Ile Val Gly Gly
            240                 245                 250 aac gaa aca cct ttg att aac att gtc atc cag gag gtc tat cgg gat           878
Asn Glu Thr Pro Leu Ile Asn Ile Val Ile Gln Glu Val Tyr Arg Asp
        255                 260                 265 ggg gtc att gcc aga gac ggg aga ctt ctt gct gga gac cag att ctt           926
Gly Val Ile Ala Arg Asp Gly Arg Leu Leu Ala Gly Asp Gln Ile Leu
    270                 275                 280 cag gtc aac aac tac aat atc agc aat gtg tcc cat aac tat gcc cga           974
Gln Val Asn Asn Tyr Asn Ile Ser Asn Val Ser His Asn Tyr Ala Arg
285                 290                 295                 300 gct gtc ctt tcc cag ccc tgc aac aca ctg cat ctt act gtg ctt cga          1022
Ala Val Leu Ser Gln Pro Cys Asn Thr Leu His Leu Thr Val Leu Arg
                305                 310                 315
```

-continued

```
gag agg cgc ttt ggc aac cga gca cac aac cat tct gat agt aac tct    1070
Glu Arg Arg Phe Gly Asn Arg Ala His Asn His Ser Asp Ser Asn Ser
        320                 325                 330 cca cga gaa gag att ttc caa gtg gct ctt cat aaa cgg gac tct ggt    1118
Pro Arg Glu Glu Ile Phe Gln Val Ala Leu His Lys Arg Asp Ser Gly
            335                 340                 345 gaa cag ctt ggc att aaa ttg gtg cga agg aca gat gag cca ggg gtt    1166
Glu Gln Leu Gly Ile Lys Leu Val Arg Arg Thr Asp Glu Pro Gly Val
350                 355                 360 ttt att ctt gac ctg ttg gaa ggg ggg ttg gct gcc cag gac ggc agg    1214
Phe Ile Leu Asp Leu Leu Glu Gly Gly Leu Ala Ala Gln Asp Gly Arg
365                 370                 375                 380 cta agc agc aat gac cga gtg ctg gcc atc aat ggg cac gac ctg aag    1262
Leu Ser Ser Asn Asp Arg Val Leu Ala Ile Asn Gly His Asp Leu Lys
            385                 390                 395 tat gga act ccg gag ctt gct gcc cag att att cag gcc agt gga gag    1310
Tyr Gly Thr Pro Glu Leu Ala Ala Gln Ile Ile Gln Ala Ser Gly Glu
                400                 405                 410 aga gtg aat tta aca att gct aga cca ggg aaa ccc cag cct ggt aac    1358
Arg Val Asn Leu Thr Ile Ala Arg Pro Gly Lys Pro Gln Pro Gly Asn
            415                 420                 425 acc att aga gaa gca gga aat cat agc agc agc agc cag cac cac aca    1406
Thr Ile Arg Glu Ala Gly Asn His Ser Ser Ser Ser Gln His His Thr
            430                 435                 440 cca cca ccg tat tat agc aga cca agc tca cat aag gat ctt act cag    1454
Pro Pro Pro Tyr Tyr Ser Arg Pro Ser Ser His Lys Asp Leu Thr Gln
445                 450                 455                 460 tgt gtt aca tgc caa gaa aaa cac att act gta aag aag gaa cca cat    1502
Cys Val Thr Cys Gln Glu Lys His Ile Thr Val Lys Lys Glu Pro His
                465                 470                 475 gaa tcc ctt ggc atg acc gtt gct ggg ggc agg gga agt aag agt ggt    1550
Glu Ser Leu Gly Met Thr Val Ala Gly Gly Arg Gly Ser Lys Ser Gly
            480                 485                 490 gag ctg ccc atc ttt gtg acc agt gtg cca ccc cat ggc tgc ctt gca    1598
Glu Leu Pro Ile Phe Val Thr Ser Val Pro Pro His Gly Cys Leu Ala
        495                 500                 505 cga gat ggc aga ata aag aga ggt gat gtg ttg cta aat atc aac ggc    1646
Arg Asp Gly Arg Ile Lys Arg Gly Asp Val Leu Leu Asn Ile Asn Gly
510                 515                 520 att gat ttg acc aat tta agt cac agt gag gca gtt gca atg ctg aaa    1694
Ile Asp Leu Thr Asn Leu Ser His Ser Glu Ala Val Ala Met Leu Lys
525                 530                 535                 540 gcc agt gcc gcg tcc cct gct gtt gcc ctt aaa gca ctt gag gtc cag    1742
Ala Ser Ala Ala Ser Pro Ala Val Ala Leu Lys Ala Leu Glu Val Gln
                545                 550                 555 att gtt gag gag gcg act cag aac gcg gag gag cag ccg agt act ttc    1790
Ile Val Glu Glu Ala Thr Gln Asn Ala Glu Glu Gln Pro Ser Thr Phe
            560                 565                 570 agc gaa aat gag tat gat gcc agt tgg tcc cca tca tgg gtc atg tgg    1838
Ser Glu Asn Glu Tyr Asp Ala Ser Trp Ser Pro Ser Trp Val Met Trp
        575                 580                 585 ctt ggg ctt ccc agc aca ctt cat agc tgc cac gat gta gtt tta cga    1886
Leu Gly Leu Pro Ser Thr Leu His Ser Cys His Asp Val Val Leu Arg
590                 595                 600 aga agt tac ttg gga agt tgg ggc ttt agt atc gtt ggt gga tat gaa    1934
Arg Ser Tyr Leu Gly Ser Trp Gly Phe Ser Ile Val Gly Gly Tyr Glu
605                 610                 615                 620 gag aac cac acc aat cag cct ttt ttc att aaa act att gtc ttg gga    1982
Glu Asn His Thr Asn Gln Pro Phe Phe Ile Lys Thr Ile Val Leu Gly
            625                 630                 635
```

```
act cct gct tat tat gat gga aga tta aag tgt ggt gac atg att gtg      2030
Thr Pro Ala Tyr Tyr Asp Gly Arg Leu Lys Cys Gly Asp Met Ile Val
            640                 645                 650 gcc gta aat ggg ctg tca acc gtg ggc atg agc cac tct gca cta gtt      2078
Ala Val Asn Gly Leu Ser Thr Val Gly Met Ser His Ser Ala Leu Val
            655                 660                 665 ccc atg ttg aag gag cag agg aac aaa gtc act ctg acc gtt att tgt      2126
Pro Met Leu Lys Glu Gln Arg Asn Lys Val Thr Leu Thr Val Ile Cys
            670                 675                 680 tgg cct ggc agc ctt gta tag attttggaaa ttggtttcaa atcttgcatc         2177
Trp Pro Gly Ser Leu Val
685             690 ttccttttt agattttga agaaaaccc tttggtttca ttgtgtttgt ggtttaggag       2237
ctgctgacac tgctggtata cacagggcca aaacccacta agattgtccg tttatgttta   2297
tttaaatggt ttcctaagtt agttacattt cttttagctt ggaaacagtc ttccactaac   2357
ctttgtgagt ttatattttc agaattcaga cttagttgtt aaa                      2400

<210> SEQ ID NO 2
<211> LENGTH: 690
<212> TYPE: PRT
<213> ORGANISM: Homo sapiens

<400> SEQUENCE: 2

Met Gly Thr Thr Ser Asp Glu Met Val Ser Val Glu Gln Thr Ser Ser
 1               5                  10                  15

Ser Ser Leu Asn Pro Leu Cys Phe Glu Cys Gly Gln Gln His Trp Thr
                20                  25                  30

Arg Glu Asn His Leu Tyr Asn Tyr Gln Asn Glu Val Asp Asp Asp Leu
            35                  40                  45

Val Cys His Ile Cys Leu Gln Pro Leu Leu Gln Pro Leu Asp Thr Pro
        50                  55                  60

Cys Gly His Thr Phe Cys Tyr Lys Cys Leu Arg Asn Phe Leu Gln Glu
65                  70                  75                  80

Lys Asp Phe Cys Pro Leu Asp Arg Lys Arg Leu His Phe Lys Leu Cys
                85                  90                  95

Lys Lys Ser Ser Ile Leu Val His Lys Leu Leu Asp Lys Leu Leu Val
            100                 105                 110

Leu Cys Pro Phe Ser Ser Val Cys Lys Asp Val Met Gln Arg Cys Asp
        115                 120                 125

Leu Glu Ala His Leu Lys Asn Arg Cys Pro Gly Ala Ser His Arg Arg
    130                 135                 140

Val Ala Leu Glu Arg Arg Lys Thr Ser Arg Thr Gln Ala Glu Ile Glu
145                 150                 155                 160

Asn Glu Asn Gly Pro Thr Leu Leu Asp Pro Ala Gly Thr Leu Ser Pro
                165                 170                 175

Glu Ala Asp Cys Leu Gly Thr Gly Ala Val Pro Val Glu Arg His Leu
            180                 185                 190

Thr Ser Ala Ser Leu Ser Thr Trp Ser Glu Pro Gly Leu Asp Asn
        195                 200                 205

Pro Ala Phe Glu Glu Ser Ala Gly Ala Asp Thr Thr Gln Gln Pro Leu
    210                 215                 220

Ser Leu Pro Glu Gly Glu Ile Thr Thr Ile Glu Ile His Arg Ser Asn
225                 230                 235                 240

Pro Tyr Ile Gln Leu Gly Ile Ser Ile Val Gly Gly Asn Glu Thr Pro
```

```
                        245                 250                 255
Leu Ile Asn Ile Val Ile Gln Glu Val Tyr Arg Asp Gly Val Ile Ala
            260                 265                 270
Arg Asp Gly Arg Leu Leu Ala Gly Asp Gln Ile Leu Gln Val Asn Asn
        275                 280                 285
Tyr Asn Ile Ser Asn Val Ser His Asn Tyr Ala Arg Ala Val Leu Ser
    290                 295                 300
Gln Pro Cys Asn Thr Leu His Leu Thr Val Leu Arg Glu Arg Arg Phe
305                 310                 315                 320
Gly Asn Arg Ala His Asn His Ser Asp Ser Asn Ser Pro Arg Glu Glu
                325                 330                 335
Ile Phe Gln Val Ala Leu His Lys Arg Asp Ser Gly Glu Gln Leu Gly
            340                 345                 350
Ile Lys Leu Val Arg Arg Thr Asp Glu Pro Gly Val Phe Ile Leu Asp
        355                 360                 365
Leu Leu Glu Gly Gly Leu Ala Ala Gln Asp Gly Arg Leu Ser Ser Asn
    370                 375                 380
Asp Arg Val Leu Ala Ile Asn Gly His Asp Leu Lys Tyr Gly Thr Pro
385                 390                 395                 400
Glu Leu Ala Ala Gln Ile Ile Gln Ala Ser Gly Glu Arg Val Asn Leu
                405                 410                 415
Thr Ile Ala Arg Pro Gly Lys Pro Gln Pro Gly Asn Thr Ile Arg Glu
            420                 425                 430
Ala Gly Asn His Ser Ser Ser Gln His His Thr Pro Pro Pro Tyr
        435                 440                 445
Tyr Ser Arg Pro Ser Ser His Lys Asp Leu Thr Gln Cys Val Thr Cys
    450                 455                 460
Gln Glu Lys His Ile Thr Val Lys Lys Glu Pro His Glu Ser Leu Gly
465                 470                 475                 480
Met Thr Val Ala Gly Gly Arg Gly Ser Lys Ser Gly Glu Leu Pro Ile
                485                 490                 495
Phe Val Thr Ser Val Pro Pro His Gly Cys Leu Ala Arg Asp Gly Arg
            500                 505                 510
Ile Lys Arg Gly Asp Val Leu Leu Asn Ile Asn Gly Ile Asp Leu Thr
        515                 520                 525
Asn Leu Ser His Ser Glu Ala Val Ala Met Leu Lys Ala Ser Ala Ala
    530                 535                 540
Ser Pro Ala Val Ala Leu Lys Ala Leu Glu Val Gln Ile Val Glu Glu
545                 550                 555                 560
Ala Thr Gln Asn Ala Glu Glu Gln Pro Ser Thr Phe Ser Glu Asn Glu
                565                 570                 575
Tyr Asp Ala Ser Trp Ser Pro Ser Trp Val Met Trp Leu Gly Leu Pro
            580                 585                 590
Ser Thr Leu His Ser Cys His Asp Val Val Leu Arg Arg Ser Tyr Leu
        595                 600                 605
Gly Ser Trp Gly Phe Ser Ile Val Gly Gly Tyr Glu Glu Asn His Thr
    610                 615                 620
Asn Gln Pro Phe Phe Ile Lys Thr Ile Val Leu Gly Thr Pro Ala Tyr
625                 630                 635                 640
Tyr Asp Gly Arg Leu Lys Cys Gly Asp Met Ile Val Ala Val Asn Gly
                645                 650                 655
Leu Ser Thr Val Gly Met Ser His Ser Ala Leu Val Pro Met Leu Lys
            660                 665                 670
```

```
Glu Gln Arg Asn Lys Val Thr Leu Thr Val Ile Cys Trp Pro Gly Ser
        675                 680                 685
Leu Val
    690
```

HUMAN EPHA9 RECEPTOR POLYPEPTIDES

FIELD OF THE INVENTION

This invention relates to newly identified polypeptides and polynucleotides encoding such polypeptides sometimes hereinafter referred to as "novel member of the EphA receptor family (EphA9)", to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to EphA9, in particular EphA9 polypeptides and EphA9 polynucleotides, recombinant materials and methods for their production. Such polypeptides and polynucleotides are of interest in relation to methods of treatment of certain diseases, including, but not limited to, Walker-Warburg syndrome (WWS), muscle-eye-brain disease (Cormand, B. et al., Am. J. Hum. Genet. 64, 126–35, 1999), Schwartz-Jampel syndrome, type I (Nicole, S. et al., Hum. Molec. Genet. 4, 1633–1636, 1995), cancer, neurodegenerative disorders, neovasculogenesis, neoangiogenesis, metastasis, neuronal plasticity disorders, disorders associated with improper or undesirable axon outgrowth or orientation, ischemia, stroke, immunological disorders, abnormal or disturbed wound healing, cardiovascular disorders, arteriosclerosis, vasculotitis, arthritis, ., hereinafter referred to as "diseases of the invention". In a further aspect, the invention relates to methods for identifying agonists and antagonists (e.g., inhibitors) using the materials provided by the invention, and treating conditions associated with EphA9 imbalance with the identified compounds. In a still further aspect, the invention relates to diagnostic assays for detecting diseases associated with inappropriate EphA9 activity or levels.

DESCRIPTION OF THE INVENTION

In a first aspect, the present invention relates to EphA9 polypeptides. Such polypeptides include:
(a) a polypeptide encoded by a polynucleotide comprising the sequence of SEQ ID NO:1 and/or SEQ ID NO:3 and/or SEQ ID NO:5 and/or SEQ ID NO:7;
(b) a polypeptide comprising a polypeptide sequence having at least 95%, 96%, 97%, 98%, or 99% identity to the polypeptide sequence of SEQ ID NO:2 and/or SEQ ID NO:4 and/or SEQ ID NO:6 and/or SEQ ID NO:8;
(c) a polypeptide comprising the polypeptide sequence of SEQ ID NO:2 and/or SEQ ID NO:4 and/or SEQ ID NO:6 and/or SEQ ID NO:8;
(d) a polypeptide having at least 95%, 96%, 97%, 98%, or 99% identity to the polypeptide sequence of SEQ ID NO:2 and/or SEQ ID NO:4 and/or SEQ ID NO:6 and/or SEQ ID NO:8;
(e) the polypeptide sequence of SEQ ID NO:2 and/or SEQ ID NO:4 and/or SEQ ID NO:6 and/or SEQ ID NO:8; and
(f) a polypeptide having or comprising a polypeptide sequence that has an Identity Index of 0.95, 0.96, 0.97, 0.98, or 0.99 compared to the polypeptide sequence of SEQ ID NO:2 and/or SEQ ID NO:4 and/or SEQ ID NO:6 and/or SEQ ID NO:8;
(g) fragments and variants of such polypeptides in (a) to (f).

Polypeptides of the present invention are believed to be members of the ephrin type A receptor family family of polypeptides. In vertebrates, the 14 Eph receptors and 8 ephrin ligands comprise two major specificity subclasses: EphA receptors bind to GPI-anchored ephrinA ligands, and EphB receptors (and EphA4) that bind ephrinB ligands, which possess a transmembrane domain and a short cytoplasmic region (Gale et al., Neuron 17, 9–19, 1996, Eph Nomenclature comittee, Cell 90, 403–404, 1997).

Expression studies have shown, that Eph receptors and ephrins are expressed in many, if not all embryonic and adult tissues (Gale et al., Neuron 17, 9–19, 1996). This data suggests that they have widespread roles. In some cases, interacting Eph receptors and ephrins have complementary domains or gradients of expression, whereas in other cases, their domains of expression overlap. Functional studies have provided important insights into the role of complementary expression in which interactions between Eph receptors and ephrins occur at boundaries or along a gradient. Juxtacrine interactions between Eph receptors and ephrins on opposing cells were initially implicated in patterning of the brain and somites, and in the process of neural cell guidance during embryonic development (for further reading refer to Mellitzer G. et al., Curr. Opin. Neurobiol. 10, 400–408, 2000, and references therein). Also, particular members of the Eph receptors and their ligands have been shown to function in the development of the vascular system and play a pivotal role in tumor angiogenesis (Illan, N. and Madri, J. A., Curr. Opin. Biotech. 10, 536–540, 1999).

Herewith we disclose the sequence information of a novel human gene encoding a new member of the Ephrin receptor family, EphA9 and the identification of 4 differential splicing isoforms. Due to the absence of amino acids known to be crucial for kinase activity it is very likely that this gene encodes an ephrin receptor with no intrinsic catalytic kinase activity (Hanks, S. K. et al., Science. 241, 42–52, 1988). Additionally, the two conserved autophosphorylation sites in the juxtamembrane region are substituted by non-phosphorylatable amino acids (Holland, S. J. et al., EMBO J. 16, 3877–3888, 1997; Hock, B. et al., Oncogene 17, 255–260, 1998).

The identified splicing isoforms affect the cytoplasmic region of the receptor. One splicing event leads to the insertion of a new domain in the juxtamembrane region of the receptor, a region known to be crucial for protein-protein interaction and signalling (see above). A further differential splicing event leads to an insertion in the middle of the ATP binding motif of the cytoplasmic kinase domain, which adds a novel stretch of 29 amino acids before it ends in a translational stop signal. Thereby, this insertion removes nearly the entire cytoplasmic kinase domain.

Herewith we disclose the sequence information of 4 differential isoforms of human EphA9.

The biological properties of the EphA9 are hereinafter referred to as "biological activity of EphA9" or "EphA9 activity". Preferably, a polypeptide of the present invention exhibits at least one biological activity of EphA9.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include a polypeptide comprising an amino acid sequence having at least 30, 50 or 100 contiguous amino acids from the amino acid sequence of SEQ ID NO: 2, or a polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of EphA9, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occuring sources, from genetically engineered host cells comprising expression systems (vide infra) or by chemical synthesis, using for instance automated peptide synthesisers, or a combination of such methods. Means for preparing such polypeptides are well understood in the art.

In a further aspect, the present invention relates to EphA9 polynucleotides. Such polynucleotides include:
(a) a polynucleotide comprising a polynucleotide sequence having at least 95%, 96%, 97%, 98%, or 99% identity to the polynucleotide squence of SEQ ID NO:1 and/or SEQ ID NO:3 and/or SEQ ID NO:5 and/or SEQ ID NO:7;
(b) a polynucleotide comprising the polynucleotide of SEQ ID NO:1 and/or SEQ ID NO:3 and/or SEQ ID NO:5 and/or SEQ ID NO:7;
(c) a polynucleotide having at least 95%, 96%, 97%, 98%, or 99% identity to the polynucleotide of SEQ ID NO:1 and/or SEQ ID NO:3 and/or SEQ ID NO:5 and/or SEQ ID NO:7;
(d) the polynucleotide of SEQ ID NO:1 and/or SEQ ID NO:3 and/or SEQ ID NO:5 and/or SEQ ID NO:7;
(e) a polynucleotide comprising a polynucleotide sequence encoding a polypeptide sequence having at least 95%, 96%, 97%, 98%, or 99% identity to the polypeptide sequence of SEQ ID NO:2 and/or SEQ ID NO:4 and/or SEQ ID NO:6 and/or SEQ ID NO:8;
(f) a polynucleotide comprising a polynucleotide sequence encoding the polypeptide of SEQ ID NO:2 and/or SEQ ID NO:4 and/or SEQ ID NO:6 and/or SEQ ID NO:8;
(g) a polynucleotide having a polynucleotide sequence encoding a polypeptide sequence having at least 95%, 96%, 97%, 98%, or 99% identity to the polypeptide sequence of SEQ ID NO:2 and/or SEQ ID NO:4 and/or SEQ ID NO:6 and/or SEQ ID NO:8;
(h) a polynucleotide encoding the polypeptide of SEQ ID NO:2 and/or SEQ ID NO:4 and/or SEQ ID NO:6 and/or SEQ ID NO:8;
(i) a polynucleotide having or comprising a polynucleotide sequence that has an Identity Index of 0.95, 0.96, 0.97, 0.98, or 0.99 compared to the polynucleotide sequence of SEQ ID NO:1 and/or SEQ ID NO:3 and/or SEQ ID NO:5 and/or SEQ ID NO:7;
(j) a polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2 and/or SEQ ID NO:4 and/or SEQ ID NO:6 and/or SEQ ID NO:8; and polynucleotides that are fragments and variants of the above mentioned polynucleotides or that are complementary to above mentioned polynucleotides, over the entire length thereof.

Preferred fragments of polynucleotides of the present invention include a polynucleotide comprising an nucleotide sequence having at least 15, 30, 50 or 100 contiguous nucleotides from the sequence of SEQ ID NO: 1, or a polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and/or SEQ ID NO:4 and/or SEQ ID NO:6 and/or SEQ ID NO:8 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:
(a) comprises an RNA transcript of the DNA sequence encoding the polypeptide of SEQ ID NO:2 and/or SEQ ID NO:4 and/or SEQ ID NO:6 and/or SEQ ID NO:8;
(b) is the RNA transcript of the DNA sequence encoding the polypeptide of SEQ ID NO:2 and/or SEQ ID NO:4 and/or SEQ ID NO:6 and/or SEQ ID NO:8;
(c) comprises an RNA transcript of the DNA sequence of SEQ ID NO:1 and/or SEQ ID NO:3 and/or SEQ ID NO:5 and/or SEQ ID NO:7; or
(d) is the RNA transcript of the DNA sequence of SEQ ID NO:1 and/or SEQ ID NO:3 and/or SEQ ID NO:5 and/or SEQ ID NO:7;
and RNA polynucleotides that are complementary thereto.

The polynucleotide sequence of SEQ ID NO:1 and/or SEQ ID NO:3 and/or SEQ ID NO:5 and/or SEQ ID NO:7 shows homology with HUMRPTK (Fox, G. M. et al., Oncogene 10, 897–905, 1995). The polynucleotide sequence of SEQ ID NO:1 and/or SEQ ID NO:3 and/or SEQ ID NO:5 and/or SEQ ID NO:7 is a cDNA sequence that encodes the polypeptide of SEQ ID NO:2 and/or SEQ ID NO:4 and/or SEQ ID NO:6 and/or SEQ ID NO:8. The polynucleotide sequence encoding the polypeptide of SEQ ID NO:2 and/or SEQ ID NO:4 and/or SEQ ID NO:6 and/or SEQ ID NO:8 may be identical to the polypeptide encoding sequence of SEQ ID NO:1 and/or SEQ ID NO:3 and/or SEQ ID NO:5 and/or SEQ ID NO:7 or it may be a sequence other than SEQ ID NO:1 and/or SEQ ID NO:3 and/or SEQ ID NO:5 and/or SEQ ID NO:7, which, as a result of the redundancy (degeneracy) of the genetic code, also encodes the polypeptide of SEQ ID NO:2 and/or SEQ ID NO:4 and/or SEQ ID NO:6 and/or SEQ ID NO:8. The polypeptide of the SEQ ID NO:2 and/or SEQ ID NO:4 and/or SEQ ID NO:6 and/or SEQ ID NO:8 is related to other proteins of the ephrin type A receptor family family, having homology and/or structural similarity with Q15375 (Fox, G. M. et al., Oncogene 10, 897–905, 1995).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one EphA9 activity.

Polynucleotides of the present invention may be obtained using standard cloning and screening techniques from a cDNA library derived from mRNA in cells of human B-cells, brain, colon tumor, colon adenocarcinoma, kidney tumor, carciniod lung, fetal lung, testis, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1 and/or SEQ ID NO:3 and/or SEQ ID NO:5 and/or SEQ ID NO:7, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1 and/or SEQ ID NO:3 and/or SEQ ID NO:5 and/or SEQ ID NO:7, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 and/or SEQ ID NO:3 and/or SEQ ID NO:5 and/or SEQ ID NO:7 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the MARATHON (trade mark) technology (Clontech Laboratories Inc.) for example, have significantly simplified the search for longer cDNAs. In the MARATHON (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al. (ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterised by the polynucleotide of SEQ ID NO:1 and/or SEQ ID NO:3 and/or SEQ ID NO:5 and/or SEQ ID NO:7 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled EphA9 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising EphA9 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit comprising:
(a) a polynucleotide of the present invention, preferably the nucleotide sequence of SEQ ID NO: 1, or a fragment or an RNA transcript thereof;
(b) a nucleotide sequence complementary to that of (a);
(c) a polypeptide, of the present invention, preferably the polypeptide of SEQ ID NO:2 and/or SEQ ID NO:4 and/or SEQ ID NO:6 and/or SEQ ID NO:8 or a fragment thereof; or
(d) an antibody to a polypeptide of the present invention, preferably to the polypeptide of SEQ ID NO:2 and/or SEQ ID NO:4 and/or SEQ ID NO:6 and/or SEQ ID NO:8.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localization studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localizations for a genomic sequence (gene fragment etc.) can be determined using Radiation Hybrid (RH) Mapping (Walter, M. Spillett, D. Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 Mar;5(3): 339–46 A radiation hybrid map of the human genome. Gyapay G, Schmitt K, Fizames C, Jones H, Vega-Czamy N, Spillett D, Muselet D, Prud'HommeJR, Dib C, Auffray C, Morissette J, Weissenbach J, Goodfellow PN). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These RCRs result in 93 scores indicating the presence or absence of the PCR product of the gene of interest. These scores are compared with scores created using PCR products from genomic sequences of known location. This comparison is conducted at the world wide web address of genome.wi.mit.edu. The gene of the present invention maps to human chromosome 1p34.1–1p34.4.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridisation techniques to clones arrayed on a grid, such as cDNA microarray hybridisation (Schena et al,
Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in B-cells, brain, colon tumor, colon adenocarcinoma, kidney tumor, carciniod lung, fetal lung, testis.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256: 495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2): Chapter 5 (1991)) or a small molecule.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a EphA9 activity in the mixture, and comparing the EphA9 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and EphA9 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and EphA9 gene. The art of constructing transgenic animals is well established. For example, the EphA9 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:
(a) a polypeptide of the present invention;
(b) a recombinant cell expressing a polypeptide of the present invention;
(c) a cell membrane expressing a polypeptide of the present invention; or
(d) an antibody to a polypeptide of the present invention;
which polypeptide is preferably that of SEQ ID NO:2 and/or SEQ ID NO:4 and/or SEQ ID NO:6 and/or SEQ ID NO:8.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an
Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1 and/or SEQ ID NO:3 and/or SEQ ID NO:5 and/or SEQ ID NO:7.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occuring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information NCBI), Bethesda, Md., USA and accessible through the home page of the NCBI at the world wide web address of ncbi.nlm.nih.gov and FASTA (Pearson W R, Methods in Enzymology, 183, 63–99, 1990; Pearson W R and Lipman D J, Proc Nat Acad Sci USA, 85 2444–2448, 1988, available as part of the Wisconsin Sequence Analysis Package).

Preferably, the BLOSUM62 amino acid substitution matrix (Henikoff S and Henikoff J G, Proc. Nat. Acad. Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the referen sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:

$n_a$ is the number of nucleotide or amino acid differences,
$x_a$ is the total number of nucleotides or amino acids in SEQ ID NO:1 and/or SEQ ID NO:3 and/or SEQ ID NO:5 and/or SEQ ID NO:7 or SEQ ID NO:2 and/or SEQ ID NO:4 and/or SEQ ID NO:6 and/or SEQ ID NO:8, respectively, I is the Identity Index,

• is the symbol for the multiplication operator, and in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-EphA9, employing an immunoglobulin Fc region as a part of a fusion protein is advantageous for performing the functional expression of Fc-EphA9 or fragments of -EphA9, to improve pharmacokinetic properties of such a fusion protein when used for therapy and to generate a dimeric EphA9. The Fc-EphA9 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding EphA9 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The invention claimed is:

1. An isolated polypeptide selected from the group consisting of:
   (a) a polypeptide encoded by a polynucleotide comprising the sequence of SEQ ID NO:1;
   (b) a polypeptide comprising a polypeptide sequence having at least 99% identity to the polypeptide sequence of SEQ ID NO:2, , wherein said polypeptide is encoded by a polynucleotide which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at 65° C.,
   wherein said polypeptide possesses ephrinA ligand binding activity; and
   (c) a polypeptide having at least 99% identity to the polypeptide sequence of SEQ ID NO:2, wherein said polypeptide is encoded by a polynucleotide which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at 65° C., wherein said polypeptide possesses ephrinA ligand binding activity.

2. The isolated polypeptide as claimed in claim 1 comprising the polypeptide sequence of SEQ ID NO:2.

3. The isolated polypeptide as claimed in claim 1 which is the polypeptide sequence of SEQ ID NO:2.

4. A fusion protein comprising an Immunoglobulin Fc-region and a polypeptide of claim 1.

5. The isolated polypeptide of claim 1, which is a polypeptide encoded by a polynucleotide comprising the nucleotide sequence of SEQ ID NO:1.

6. The isolated polypeptide as claimed in claim 1 which is a polypeptide comprising a polypeptide sequence having at least 99% identity to the polypeptide sequence of SEQ ID NO:2, and which is encoded by a polynucleotide which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at 65° C., wherein said polypeptide possesses ephrinA ligand binding activity.

7. The isolated polypeptide as claimed in claim 1 which is a polypeptide having at least 99% identity to the polypeptide sequence of SEQ ID NO:2, and which is encoded by a polynucleotide which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at 65° C., wherein said polypeptide possesses ephrinA ligand binding activity.

* * * * *

UNITED STATES PATENT AND TRADEMARK OFFICE
CERTIFICATE OF CORRECTION

PATENT NO. : 7,074,899 B2
APPLICATION NO. : 10/333789
DATED : July 11, 2006
INVENTOR(S) : Hock et al.

Page 1 of 1

It is certified that error appears in the above-identified patent and that said Letters Patent is hereby corrected as shown below:

Column 27, line 18, reads "NO:2, , wherein" should read -- NO:2, wherein --

Signed and Sealed this

Thirteenth Day of February, 2007

JON W. DUDAS
*Director of the United States Patent and Trademark Office*